United States Patent
Cook et al.

[11] Patent Number: 5,957,914
[45] Date of Patent: Sep. 28, 1999

[54] PHOTO OPTIC BREAKDOWN PROBE

[75] Inventors: Kenneth Price Cook, Blue Bell; Robert Michael Bross, Ivyland, both of Pa.

[73] Assignee: Surgical Laser Technologies, Inc., Montgomeryville, Pa.

[21] Appl. No.: 08/925,368

[22] Filed: Sep. 8, 1997

Related U.S. Application Data

[63] Continuation of application No. 08/177,782, Jan. 6, 1994, abandoned, which is a continuation of application No. 07/935,665, Aug. 25, 1992, abandoned, which is a continuation of application No. 07/540,085, Jun. 19, 1990, abandoned.

[51] Int. Cl.$^6$ .................................................. A61N 5/06
[52] U.S. Cl. ........................... 606/6; 606/2; 606/10; 606/15
[58] Field of Search ............................... 606/2, 2.5, 3–18

[56] References Cited

U.S. PATENT DOCUMENTS

| | | | |
|---|---|---|---|
| 4,559,942 | 12/1985 | Eisenberg | 606/6 |
| 4,583,539 | 4/1986 | Karlin et al. | 606/4 |
| 4,608,979 | 9/1986 | Breidenthal et al. | |
| 4,662,368 | 5/1987 | Hussein et al. | 606/7 |
| 4,672,961 | 6/1987 | Davies | 606/7 |
| 4,694,828 | 9/1987 | Eichenbaum | 606/6 |
| 4,887,600 | 12/1989 | Watson et al. | |
| 4,932,954 | 6/1990 | Wondrazek et al. | |
| 5,041,121 | 8/1991 | Wondrazek et al. | |
| 5,224,942 | 7/1993 | Beuchat et al. | |
| 5,257,988 | 11/1993 | L'Esperance, Jr. | |
| 5,324,282 | 6/1994 | Dodick | |

OTHER PUBLICATIONS

"Contact Transscleral Continuous Wave Neodymuim: YAG Laser Cyclophotocoagulation" by Schuman et al; Opthalmology vol. 97 No. 5 pp. 571–580.

"Two Experimental Proceedures Could Replace Phaco" by Cella; Ophthalmology Times; Dec. 15, 1989 pp. 1 & 6.

*Primary Examiner*—David Shay
*Attorney, Agent, or Firm*—Seidel, Gonda, Lavorgna & Monaco

[57] ABSTRACT

A laser photo optic breakdown probe and handpiece system especially suited for small-incision cataract removal including an optical fiber through which a pulsed source of laser energy is delivered to a target spaced from the distal end of the fiber. The fiber is routed through a first guide tube with the target mounted at an angle on the end thereof. Holes are provided in the guide tube for the flow of infusion fluid therethrough. A second aspiration tube surrounds and provides rigidity to the guide tube, shields the distal end of the fiber and target, and serves as a channel for aspirated fluids and dislodged cataractous material. The guide tube is affixed to a transfer housing to which infusion and aspiration connections are made. The aspiration tube forms part of a handle assembly which is detachably coupled to the transfer housing.

5 Claims, 2 Drawing Sheets

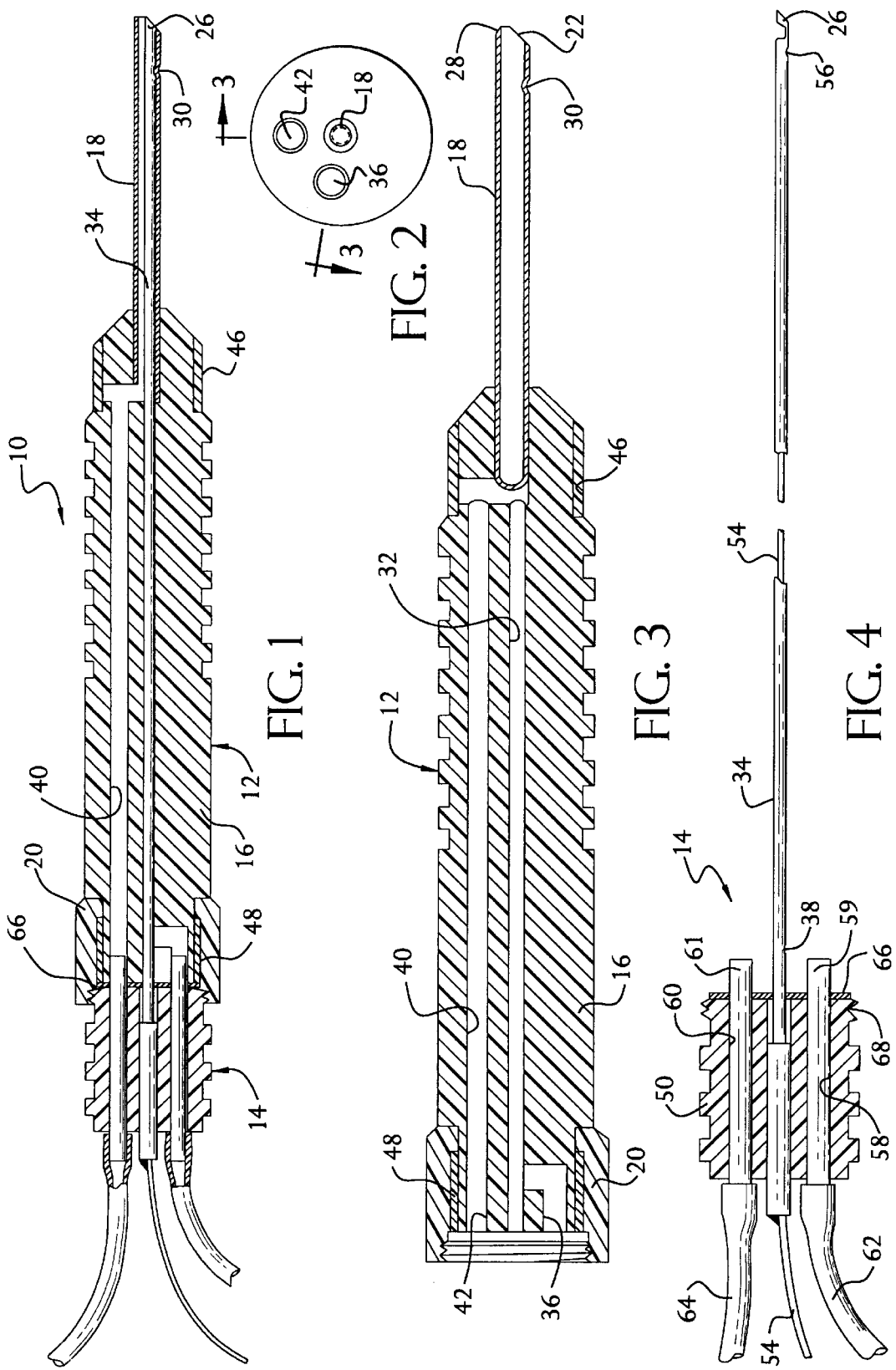

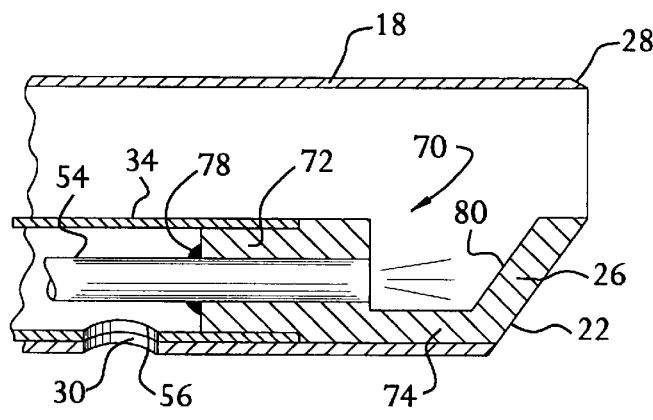
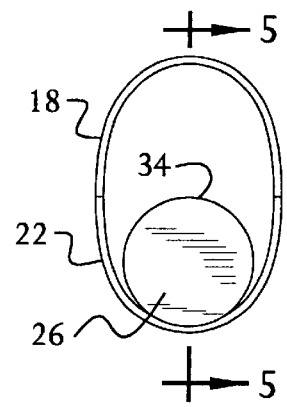
FIG. 5    FIG. 6
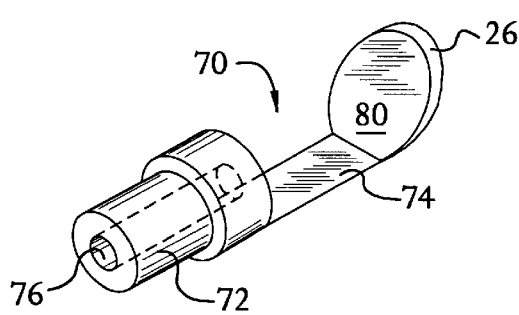
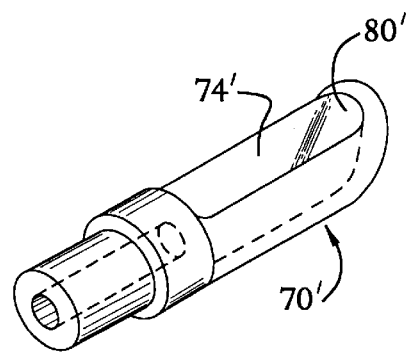
FIG. 7    FIG. 8
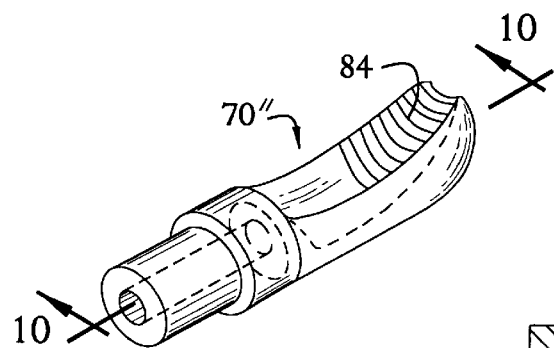
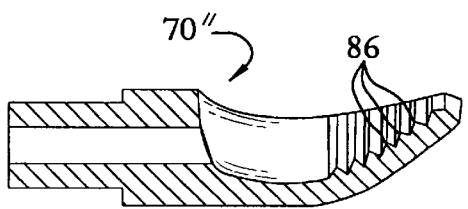
FIG. 9    FIG. 10

PHOTO OPTIC BREAKDOWN PROBE

This is a continuation of application(s) Ser. No. 08/177,782 filed on Jan. 6, 1994 which is a continuation of Ser. No. 07/935,665 filed on Aug. 25, 1992, which is a continuation of Ser. No. 07/540,085 filed on Jun. 19, 1990, all now abandoned.

BACKGROUND OF THE INVENTION

The present invention relates to a laser surgical probe and handpiece system and, more particularly, to a laser instrument adapted for the treatment of cataracts and similar ophthalmological surgical procedures.

The present probe defines a small-incision ophthalmology device generally intended to replace current ultrasonic phacoemulsification instruments. The probe is integrated into a handpiece system which serves, first, as a handle spaced in close proximity to the operative probe tip and, second, as a fluid and air interface system.

In this latter connection, cataract surgery results in the dislodging of nuclear lens material which must be evacuated, in turn, through a suction or aspiration port immediately adjacent the active laser tip region. As is well known, the removal of eye material and fluid, without the concurrent infusion of an equal volume of fluid, may result in the collapse or other damage to the eye. Consequently, the present probe and handpiece provides, in addition to its principal cataract dislodging function, the complementary functions of aspiration and infusion.

The use of lasers in ophthalmology is known, for example, in the treatment of retinal bleeding. This procedure involves the focusing of an argon or argon/krypton laser, generally with the aid of a slit lamp through the front of the eye, onto the retina where bleeding has been observed thereby coagulating or cauterizing such bleeding spots.

Retinal bleeding has also been treated by endophotocoagulation, a procedure in which an optical quartz fiber, for the transmission of laser energy, is introduced into the eye through the vitreous material of the posterior chamber. This coagulation technique is generally combined with aspiration/infusion whereby diseased vitreous material is removed and replaced by an appropriate saline solution.

Lasers have also found application in the treatment of glaucoma. As recently reported and summarized in *Ophthalmology* (May 1990, Volume 97, No. 5), Nd:Yag laser techniques, in particular the use of contact laser probes, have immediately and significantly reduced intraocular pressure, the underlying pathology of glaucoma. Importantly, such improvements have been of a lasting nature.

A not infrequent side-effect of cataract surgery is the formation of what is commonly referred to as a "secondary cataract". Removal of "secondary cataracts" represents another ophthalmic disorder in which lasers have found application. Secondary cataracts are, in reality, the darkening of the posterior capsule or membrane which separates the lens from the vitreous fluid comprising the posterior cavity of the eye. In the healthy eye this capsule is transparent. Typically argon lasers are employed in the disintegration of this membrane material.

Except for the removal of these "secondary cataracts", lasers have not previously been utilized successfully in the treatment of the true cataract condition. Rather, conventional cataract treatment has required the surgical removal of the diseased lens, 'expressed' through a comparatively large incision. More recently, the above-noted phacoemulsification procedure has been developed which breaks-up, then removes disintegrated nucleus and other lens material. Phacoemulsification, although facilitating cataract removal through a smaller incision, has been know to cause deleterious postoperative complications.

The present invention, therefore, represents the first direct and successful application of laser technology to the treatment of the cataract condition. Advantageously, the present apparatus and procedure (referred to as laser phacolysis) permits minimally invasive cataract removal, i.e. through a substantially smaller incision than that required for conventional procedures and, importantly, without various of the deleterious effects of phacoemulsification.

Laser phacolysis, however, does not utilize laser energy in its conventional surgical context, that is, as a medium for the direct cutting of tissue. Rather, laser energy is propagated in the conventional manner through an optical fiber to the probe herein described. The probe converts this optical energy into an acoustic shock wave which, in turn, causes the mechanical cutting or disintegration or the cataractous nuclear lens material.

More specifically, pulsed Nd:Yag laser energy is directed against a target spaced within a few millimeters from the distal end of the optical fiber. The target may be of planar or concave contour and is oriented at an angle to the incoming laser beam such that the angle of laser incidence is, for example, in the order of 45 degrees.

The target is preferably surrounded by a narrow diameter tubular housing which serves, first, to define an aspiration inlet channel and, second, as a shield to protect the patient as well as the surgeon against the otherwise uncontained reflection of laser energy. An orifice is provided in the distal forward end of the tubular housing through which the nuclear material may be withdrawn and evacuated from the lens. This forward end region of the housing may be pointed or sharpened to enhance dislodgement of the nuclear material. As presently understood, such dislodgement is occasioned not only through the direct action of the acoustic energy wave, but, by the micro-mechanical reciprocal oscillation of the probe, induced by the periodic pulsing of the laser.

A separate infusion passage and port is provided through which a saline or other solution may be introduced as required to replenish eye fluids aspirated during the cataract removal procedure.

BRIEF DESCRIPTION OF THE DRAWINGS

FIG. 1 is a front elevation view, taken in section along line 3—3 of FIG. 2, of the assembled laser optical breakdown probe and handpiece of the present invention;

FIG. 2 is a left elevation view of the transfer housing portion of the present invention illustrating the asymmetrical arrangement of the infusion and aspiration channels;

FIG. 3 is a front elevation view, taken in section along line 3—3 of FIG. 2, of the handle portion of the optical breakdown probe and handpiece of FIG. 1;

FIG. 4 is a front elevation view, taken in section along line 3—3 of FIG. 2, of the transfer housing portion of the optical breakdown probe and handpiece of FIG. 1;

FIG. 5 is an enlarged sectional view, taken along line 5—5 of FIG. 6, of the distal end of the optical breakdown probe and handpiece of FIG. 1;

FIG. 6 is a right elevation view of the infusion and aspiration tubes of the optical breakdown probe and handpiece of FIG. 1;

FIG. 7 is a perspective view of the target member of the optical breakdown probe and handpiece of FIG. 1 as shown in more detail in FIG. 5;

FIG. 8 is a perspective view of an alternative embodiment for the target member of the present probe and handpiece;

FIG. 9 is a perspective view of another alternative embodiment for the target member of the present probe and handpiece; and, FIG. 10 is a sectional view taken along line 10—10 of FIG. 9 showing in more detail the laser target face.

DESCRIPTION OF THE PREFERRED EMBODIMENT

FIG. 1 illustrates the complete photo optical breakdown probe 10 of the present invention including a handle 12 and transfer housing 14 each separately illustrated in respective FIGS. 3 and 4.

Handle 12 includes a molded plastic body 16 having a stainless steel (for example 303 stainless) tubular aspiration tube 18 affixed to, and extending axially from, the distal end thereof. A captured nut 20 is provided for coupling the handle and transfer housing members (FIG. 1).

The aspiration tube 18 is preferably of elliptical cross section (FIG. 6). Tube 18 may be fabricated by placing a 0.056 inch diameter rod within a standard 0.083 inch diameter hypodermic needle, thereafter, by compressing the needle until a minor elliptical diameter corresponding to that of the rod is achieved.

The distal end of aspiration tube 18 is detailed in FIGS. 3, 5 and 6 wherein a backwardly angled or recessed slope 22 is shown machined at the bottom of the otherwise transversely severed tubular aspiration tube. This sloped region 22 generally conforms to the angled laser target 26 discussed in more detail below.

The upper and most forward portion of the elliptical tube 18 may be machined to a sharpened edge 28 to augment the dislodging of nuclear lens material. An aperture 30 is provided in the lower forward region of the tube 18 to facilitate passage of infusion fluids.

Referring again to FIG. 3, a circular channel 32 is molded along the central longitudinal axis of handle body 16 thereby defining a linear passage through which optical guide tube 34 is snugly received during probe assembly (see FIG. 1). This channel is additionally in fluid communication with an infusion port 36, which port defines a circular opening in the proximal end of the body parallel to, but offset from, the body axis. Infusion fluid entering port 36 passes into the optical guide tube 34 through a hole 38 therein (FIGS. 1 and 3), in turn, exiting at the distal end of the probe through hole 56 as described in more detail below.

A second or aspiration channel 40 is molded into handle body 16. This channel provides fluid communication between a corresponding second or aspiration port 42, at the proximal end of the handle body, and the tubular aspiration tube 18 which tube extends from the distal end of the handle body. In this manner fluid and dislodged nuclear lens material may be evacuated from the eye through the aspiration tube, in turn, outwardly through channel 40 and port 42.

The infusion and aspiration ports 36, 42 are preferably disposed in a non-symmetrical manner relative to the central axis of the handle body 16 (FIG. 2) and therefore serve the further function of aligning the transfer housing 14 and handle 12 upon insertion and assembly of the former into the latter. In this manner the transfer housing 14 inlet and outlet holes 38,56 and laser target 26 (described below) are properly oriented with respect to the corresponding structural elements of the mated handle 12.

It will be noted that material drawn into the aspiration tube 18 is precluded from entering guide tube channel 32 by reason of a relatively close fit between the guide tube 34 and channel 32. Alternatively, a sealant may by applied around the guide tube to preclude any aspirant flow other than through the prescribed aspiration channel 40.

A pair of annular rings 46 and 48 are placed around the handle body, respectively, at the forward and rearward ends thereof. These rings serve to seal openings to channels 32 and 40 caused by the removal of tooling core members during the injection molding fabrication process. Ring 48 additionally functions as a locking or restraining collar for the threaded coupling nut 20. Nut 20 is thereby free to rotate on handle body 16 and is so rotated to secure the handle to the transfer housing.

FIG. 4 best illustrates the transfer housing 14 portion of the present optical breakdown probe. Transfer housing 14 includes the previously noted elongate optical guide tube 34 which tube is rigidly affixed to, and extends from and along the central axis of a molded plastic base member 50. Guide tube 34 is preferably fabricated from 303 stainless material and may be a conventional hypodermic-type needle of 0.042 inches i.d. The guide tube 34 is flexed or otherwise oriented downwardly from the central axis thereby biasing and seating the distal end thereof against the lower portion of the elliptical aspiration tube 18 as shown in FIGS. 5 and 6.

A conventional optical fiber 54 of, for example, 300$\mu$ diameter is positioned within the guide tube 34 and extends from the distal end of probe 10, at a point approximately 1–3 mm from target 26 (FIG. 5), rearwardly of the transfer housing 14 to a source of laser energy.

Guide tube 34 additionally serves as the conduit through which infusion fluid is conveyed from the rear of the handle body to the operative situs, entering as previously described at hole 38 and exiting through a hole 56 adjacent the distal end thereof. The transfer housing and handle are keyed, as discussed above, such that the respective guide tube and aspiration tube holes 56 and 30 are in alignment thereby assuring the uninhibited egress of infusion fluid from probe 10.

A pair of longitudinal passages 58 and 60 are formed within and through the transfer housing base member 50 and are adapted to receive a corresponding pair of metal tubes 59 and 61 therein. These tubes 59,61 extend outwardly from both ends of the base member 50 and serve to interconnect respective infusion and aspiration hoses 62,64 with corresponding ports 36,42 in the handle body. More specifically, hoses 62,64 may be slid-over the proximal ends of tubes 59,61 while the remaining opposed ends of these tubes are received within, and function to orient, the handle as previously discussed.

Alternatively, a single aspiration port 42 may be provided on the handle body 16 with the infusion port 36 being omitted. In this alternative arrangement, the infusion inlet hole 38 would be repositioned within the base member 50 thereby permitting a direct fluid connection between passage 58 and the guide tube 34 entirely within the base member. In this embodiment, the single remaining port 42 within the handle body 16 would serve as the assembly alignment key.

A gasket 66 may be placed between the base member and housing body to seal this interface against any loss of infusion or aspiration fluid. Threads 68 at the forward end of the base member receive the coupling nut 20 thereby securely interconnecting the transfer housing and handle members as shown in FIG. 1.

It will be appreciated that the two-piece arrangement of the present invention, specifically the detachable handle and transfer housing structure described above, facilitates improved probe servicing. For example, the titanium targets, which are known to wear, may require replacement after several surgical procedures. These targets are more easily replaced by removal of the transfer housing, including guide tube 34 and target 26, from the handle and aspiration tube. It will be understood, however, that the present invention is not limited to such two-member systems and additionally contemplates a probe and handpiece arrangement of unitary construction in which both tubes are affixed to a common handle assembly.

FIGS. 5 and 6 best illustrate the distal or operative end of probe 10 with FIG. 7 providing a perpsective view of the target member 70 shown therein. FIG. 8 illustrates an alternative embodiment for the target member.

As previously described, guide tube 34 is rotationally indexed and downwardly biased thereby forcing the distal end of tube 34 to seat in the lower portion of the aspiration tube 18 (FIG. 6) with, importantly, the respective infusion holes 30 and 56 in fluid passing alignment (FIG. 5).

The target member 70 is preferably machined or otherwise fabricated of titanium and includes integral anchor body 72, target 26, and support member 74, the support member serving to rigidly retain the target and anchor body in spaced relationship.

The anchor body is of cylindrical form and is adapted for a snug interference fit within the end of the guide tube 34. A bore 76 is provided along and through the central axis thereof into which the distal end of optical fiber 54 is positioned and, as required, secured by cement 78 (FIG. 5). More specifically, the distal end of the optical fiber is spaced between about 1 and 3 mm, preferably 1.5 mm, from the target 26.

The target defines a planar surface 80 which is disposed at an angle, for example 45 degrees, to the axis of the optical fiber and impinging laser beam. In this manner the laser energy is neither reflected back to the fiber (which reflection could damage the fiber) nor permitted to freely exit the probe.

In fact the target, although positioned at the extreme end of the aspiration tube 18, remains within the tube thereby affording shielding and protection to the surrounding healthy tissue and attending personnel.

A source of pulsed laser energy is coupled to the proximal end of the fiber. Pulse energy levels between a fraction of a millijoule and several millijoules have been utilized. A pulse repetition rate of about 10 pulses per second is typical, although not critical.

The laser pulse, upon striking the optically opaque titanium target "breaks down", i.e. is converted in form, ultimately to that of a sonic or shock wave. This sonic wave propagates outwardly from the point of laser target impact, generally transversely across and along the major diameter of the elliptical aspiration tube until engaging nuclear lens material adjacent or aspirated into the tube whereby such material is disintegrated and removed by the continuing aspiration process.

The positive qualities of the present probe are believed to be further enhanced by sharpening the distal end 28 of the aspiration tube, generally at a point opposed to that of the target. In this manner, any micro-mechanical reciprocal motion of the probe, as occasioned by the conversion of the pulsed laser energy into mechanical energy, contributes to the nuclear material cutting or dislodging function.

FIG. 8 is an alternative arrangement of the target member 70' differing in two principal respects from the target member 70 of FIGS. 5 and 7. First, the target surface 80' is concave which causes a focusing or general alteration of the sonic energy wavefront pattern. Second, the support member 74' defines a U-shaped structure of substantially improved strength. The target is, in short, more rigidly affixed to the guide tube 34 thereby obviating unanticipated and energy-dissipating inelastic movements thereof.

FIGS. 9 and 10 illustration yet another arrangement for the target member 70" in which the target surface 84 defines a saw-tooth contour having a plurality of faces 86 angled, as previously described, with respect to the impinging laser beam.

What is claimed:

1. A surgical laser optical breakdown probe for targeting and fracturing tissue comprising:

(a) a laser for producing laser energy in pulses sufficient to be optically broken down into mechanical shock waves that will target and fracture tissue material that is to be surgically treated;

(b) a first tubular member having a longitudinal axis and a distal end portion;

(c) a laser fiber connected at a first end to said laser and extending within said first tubular member and longitudinally to said distal end portion of said first tubular member, said laser fiber having a longitudinal axis and a distal end remote from said first end;

(d) a second tubular member disposed around said first tubular member and having a distal end portion at least partially extending beyond the distal end portion of said first tubular member and surrounding the distal end of said laser fiber;

(e) a target at the distal end portions of said first and second tubular members and adjacent to said distal end of the laser fiber;

(f) said target having a saw-toothed laser energy engagement surface for causing laser energy emitted from said laser fiber onto said surface to be broken down and converted into mechanical shock waves, said surface being oriented obliquely with respect to the distal end of the laser fiber such that the laser energy impinging thereon does not freely exit the probe;

(g) cavity means bounded by at least said surface, the distal end portion of the second tubular member, the distal end portion of the first tubular member, and the distal end of said laser fiber;

(h) said cavity means having a port framed at least by the distal end of the target and that portion of the distal end of the second tubular member which is opposite the target, such port providing means for receiving into said cavity dislodged tissue material that is to be treated, said cavity and port being radially displaced from the longitudinal axis of said laser fiber;

(i) said cavity means thereby providing an operating situs containing said mechanical shock waves that are propagated thereto and that target and fracture tissue material received therein;

(j) an aspirating passage extending longitudinally within said second tubular member and in communication with said cavity;

(k) said second tubular member and said target being sharpened where they form a part of the rim of said port, such that said sharpened portions vibrate due to the optical breakdown of the laser energy on said target engagement surface and, when brought into contact with the tissue material to be treated, cause it to dislodge and be drawn into the operating situs.

2. A laser optical breakdown probe according to claim 1, wherein the second tubular member has a longitudinal axis parallel with the longitudinal axis of the first tubular member, the probe further comprising:

(l) a handle assembly having a longitudinal axis coaxial with the longitudinal axes of the first and second tubular members, the handle assembly being affixed around a portion of the first and second tubular members, the handle assembly having a passage defined along its longitudinal axis through which the optical fiber may pass, whereby the handle assembly serves to properly orient and retain the first and second tubular members and also serves as a member by which a surgeon may hold and direct the probe.

3. A laser optical breakdown probe according to claim 1, further comprising (l) a handle assembly including a transfer housing and a body, the first tubular member being affixed to and extending from the transfer housing, the transfer housing having a passage defined therein through which the optical fiber may pass, the second tubular member being affixed to and extending from the body; and (m) means for detachably interconnecting the housing and body whereby the first tubular member and target are removable from within the second tubular member for service or repair.

4. A laser optical breakdown probe according to claim 3, further comprising (n) a first fluid inlet means on the transfer housing and an orifice at the distal end portion of the first tubular member, the first fluid inlet means being in fluid communication with the first tubular member, thereby allowing infusion fluid entering the first fluid inlet means to be provided at the operating situs; and (o) second inlet means on the transfer housing, the second inlet means being in fluid communication with the second tubular member, thereby allowing fluid and dislodged nuclear material to be withdrawn from the operating situs through the aspirating passage in the second tubular member.

5. A laser optical breakdown probe according to claim 3, wherein the second tubular member has a longitudinal axis coaxial with the longitudinal axis of the first tubular member, the probe further comprising:

(n) a handle assembly having a longitudinal axis coaxial with the longitudinal axes of the first and second tubular members, the handle assembly being affixed around a portion of the first and second tubular members, the handle assembly having a passage defined along its longitudinal axis through which the optical fiber may pass, whereby the handle assembly serves to properly orient and retain the first and second tubular members and also serves as a member by which a surgeon may hold and direct the probe.

\* \* \* \* \*